(12) United States Patent
Yachia et al.

(10) Patent No.: US 6,746,421 B2
(45) Date of Patent: *Jun. 8, 2004

(54) INTRAVESICAL DEVICE

(75) Inventors: Daniel Yachia, Herzliya on Sea (IL); Eran Hirszowicz, Ramat-Chen (IL)

(73) Assignee: Innoventions Inc., Edina, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/363,287

(22) Filed: Jul. 28, 1999

(65) Prior Publication Data

US 2002/0055730 A1 May 9, 2002

Related U.S. Application Data

(63) Continuation-in-part of application No. 09/268,109, filed on Mar. 15, 1999, now Pat. No. 6,293,923.

(51) Int. Cl.[7] ........................ A61M 11/00; A61M 31/00; A61F 2/00
(52) U.S. Cl. .................... 604/93.01; 600/29; 604/517
(58) Field of Search ................ 604/96.01, 93.01, 604/103.03, 215, 337, 41, 907, 890.1, 892.1; 600/29–32; 424/422–426, 430–433; 128/885, DIG. 25

(56) References Cited

U.S. PATENT DOCUMENTS

| | | | |
|---|---|---|---|
| 4,055,178 A * | 10/1977 | Harrigan | 128/260 |
| 4,607,639 A | 8/1986 | Tanagho et al. | 128/419 E |
| 4,804,375 A | 2/1989 | Robertson | 604/323 |
| 4,834,704 A | 5/1989 | Reinicke | 604/51 |
| 4,850,963 A | 7/1989 | Sparks et al. | 600/29 |
| 4,871,542 A | 10/1989 | Vilhardt | 424/423 |
| 4,925,446 A | 5/1990 | Garay et al. | 604/96 |
| 5,019,032 A | 5/1991 | Robertson | 600/29 |
| 5,030,199 A | 7/1991 | Barwick et al. | 600/29 |
| 5,188,109 A | 2/1993 | Saito | 128/635 |
| 5,234,409 A | 8/1993 | Goldberg | 604/96 |
| 5,334,197 A * | 8/1994 | Kriesel et al. | 604/132 |
| 5,443,470 A | 8/1995 | Stern et al. | 607/98 |
| 5,472,441 A | 12/1995 | Edwards et al. | 606/41 |
| 5,579,781 A | 12/1996 | Cooke | 128/733 |
| 5,604,531 A | 2/1997 | Iddan et al. | 348/76 |
| 5,653,689 A | 8/1997 | Buelna et al. | 604/103.9 |
| 5,704,353 A | 1/1998 | Kalb et al. | 128/634 |
| 5,732,714 A * | 3/1998 | Morrissey et al. | 128/846 |
| 5,749,845 A | 5/1998 | Hildebrand et al. | 604/21 |
| 5,762,599 A | 6/1998 | Sohn | 600/30 |
| 5,800,478 A | 9/1998 | Chen et al. | 607/88 |
| 5,806,527 A | 9/1998 | Borodulin et al. | 128/885 |
| 5,984,860 A | 11/1999 | Shan | 600/116 |
| 5,989,230 A | 11/1999 | Frassica | 604/264 |
| 6,066,088 A | 5/2000 | Davis | 600/29 |
| 6,139,535 A | 10/2000 | Greelis et al. | 604/500 |

FOREIGN PATENT DOCUMENTS

| | | |
|---|---|---|
| EP | 0667115 | 8/1995 |
| FR | 2693116 | 1/1994 |
| WO | 0024337 | 5/2000 |
| WO | 0054702 | 9/2000 |

* cited by examiner

Primary Examiner—Michael J. Hayes
(74) Attorney, Agent, or Firm—Ladas & Parry

(57) ABSTRACT

An expandable umbrella-like device for insertion into the urinary bladder of an individual. The umbrella may be used in the treatment of urinary incontinence or in treating urinary bladder dysfunctions.

7 Claims, 8 Drawing Sheets

INTRAVESICAL DEVICE

This application is being filed as a continuation-in-part to U.S. application Ser. No. 09/268,109 filed on Mar. 15, 1999, now U.S. Pat. No. 6,293,923.

FIELD OF THE INVENTION

The invention is in the field of medical devices. More specifically, the invention relates to devices for the treatment of urinary incontinence.

BACKGROUND OF THE INVENTION

Several disorders of the urinary tract are known. Among these are urinary incontinence, chronic urinary tract infections, urinary bladder tumors.
Urinary Incontinence Urinary incontinence mostly affects women (approximately 10 million in the U.S.A. alone) primarily after childbirth or due to old age. In men, urinary incontinence often occurs as a complication of surgery or old age (approximately 3 million in the U.S.A.).

Incontinence has serious economic, health, social and psychological consequences. Its estimated cost to the health system in the United States in 1993 was US $16 billion. It leads to chronic and severe skin irritation in the genital area, an increase in urinary infections and urosepsis. Fear of incontinence and odors in public cause incontinent people to severely restrict their social activities. The impact on the mental health of the affected people may be even more devastating than the social and health consequences. They suffer severe embarrassment, loss of self-esteem, depression and anxiety.

Urinary incontinence can be divided into four groups:

Stress Incontinence—is the involuntary release of urine due to a sudden increase in the intra-abdominal pressure caused by laughing, sneezing, coughing, running, etc. This is the most common type of incontinence and in women may be the result of anatomical changes in the pelvic organs after childbirth, estrogen deficiency, unsuccessful surgical repairs for incontinence or pelvic irradiation. In men, it often happens after surgery for benign enlargement of the prostate gland or after radical removal of the prostate.
Total Incontinence—is the continuous leak of urine entering the bladder due 15 to failure of the sphincteric muscles.
Urge Incontinence—is involuntary loss of urine due to involuntary bladder contractions. This type of incontinence mostly affects the elderly who leak until they reach a toilet.
Mixed Incontinence—is a combination of stress and urge incontinence. This condition is more common in elderly women than men.

Ideally, treatment of incontinence should provide permanent dryness and is easy to perform.

Pharmacological treatments of bladder dysfunctions are based either on estrogen replacement for treating postmenopausal vaginal and urethral atrophy or on agents affecting the tonus of the bladder muscle. Since affected elderly women suffer from both hormonal deficiency and urinary incontinence, both types of agents are usually prescribed simultaneously.

Surgical treatments are based on restoring the anatomical changes causing the incontinence. Although in the short-term most surgical procedures restore continence, the long-term prognosis is usually unsatisfactory. Moreover, surgery entails morbidity and high expenses.

Conservative/behavioral treatments are based on pelvic floor muscle exercises, bladder training, biofeedback, vaginal cones, low-frequency electrostimulation of pelvic floor muscles, intravaginal bladder neck support pessaries, urethral meatus suction cups and intraurethral devices. Conservative treatments are time consuming and require the patients' understanding, cooperation and persistence.

Devices which have been used to obtain almost immediate dryness in incontinent people can be divided into two groups:
(1) Urethral Plugs/Inserts These comprise a flexible rod having, a 14 Ch. (approximately 4.5 mm) diameter and a length adjusted to fit the length of the patient's urethra. The rod has an inflatable balloon on its bladder end and a flange at other end. After insertion of the device, the balloon is inflated in the bladder. The balloon and the flange, maintain the device in its proper position within the urethra. The balloon and rod form a mechanical barrier to retain the urine within the bladder. The balloon must be deflated and the device removed and discarded prior to voiding. Such inserts are known in the art, for example, the device known as RELIANCE produced by UroMed Corp., U.S.A. Since inserts are discarded after each voiding and replaced with a new one by the patient, manual dexterity of the patient is required. Insertion of an insert into a female has the risk of pushing vaginal and perineal bacteria into the bladder and insertion of an insert a few times a day increases this risk. The inconvenience of removing and inserting a new device and its costs, in addition to the infection risk, are the major disadvantages of these devices.
(2) Valve Catheters These comprise a tube with a valve at one end. The bladder end of the device typically has a balloon or flanges for retaining the device in place and a flange at the other end to prevent migration into the bladder. The valve is opened for voiding through the lumen of the catheter with the help of an external magnet. The tube typically has a 18 Ch. (6 mm.) to 20 Ch.(approximately 7 mm) diameter and a length adjusted to fit the patient's urethra. For male incontinence, an active intraurethral Foley-type catheter is used. This device has a retaining, balloon at its bladder end and another smaller balloon under the prostate for fixing the device in place. The magnet activated valve is situated at the end of the device near the distal end of the urethra. Active inserts are typically left indwelling up to 4 weeks and are then replaced.

Examples of such catheters are disclosed in U.S. Pat. Nos. 5,030,199 and 5,234,409. Valve catheters are more convenient for the patient than the inserts; however, in females they cause ascending infection because they connect the bladder with the vulva which is rich in pathogenic bacteria, especially *Escherichia Coli*. Even with continuous use of antibiotics, infection is inevitable in the majority of cases. During prolonged use of cathetersor inserts in female patients, a relaxation of the urethra occurs and the patients may start to leak around the device. Unfortunately valve catheters and inserts are unavailable in increasing diameters.

A significant disadvantage of both the inserts and the valve catheters is the discomfort felt by the patient especially when sitting and during sexual intercourse (felt by the patient and the partner).

The present invention therefore provides a device for the treatment of urinary incontinence in which the disadvantages of the prior art devices are substantially reduced or eliminated.

Urinary Tract Infections

Nearly half of all women experience urinary tract infection (UTI) at some point in their lifetime and most of these infections are confined to the bladder. Isolated UTIs can be treated by short and effective antibiotic treatment. However, recurrent UTIs often occur in women due to antibiotic resistant bacteria. In this case complicated infections often exhibit multidrug resistance and necessitate longer antimicrobial drug administrations.

Treatment of UTI often requires urinary levels of antimicrobial drugs that are several hundred times greater than those allowable in the blood. Many antibacterials cannot be used in UTI because, when taken orally or intravenously, they do not attain the required concentration in the urine, without exceeding the allowable limit in the blood. It would therefore be desirable to be able to continuously introduce antimicrobial drugs continuously and directly into the bladder.

Bladder Tumors

Even after resection, bladder tumors may not only recur but may also invade deeper in the bladder wall. Due to the heterogenity of these tumors (from low-grade tumors showing a benign course to highly malignant high-grade tumors), there does not exist a single approach to the surveillance and treatment of these tumors. Intravesical drug therapies are often used for reducing tumor recurrence. In this approach, an immunotherapeutic or chemotherapeutic agent is inserted into the bladder through a catheter. This treatment is typically repeated once a week for 6 weeks and then once a month for a period of 6–12 months. However, periodic treatment has not been established as being effective in altering the progression of the tumor. Continuous local treatment with chemotherapeutic or radioactive materials may treat or prevent not only superficial tumors but also deep tumors as well. It would therefore be desirable to be able to introduce antitumoral drugs continuously and directly into the bladder.

Bladder Dysfunction

During filling, the bladder muscle relaxes for keeping the intravesical pressure low while it contracts for voiding. Certain diseases such as spinal cord injuries, diabetes, multiple sclerosis, or hormonal changes after menopause or old age in both sexes may cause a hypo contractility or, paradoxically, hyper contractility of the muscle. In atonic bladder, pharmacological treatment is not very effective. In hyperreflexic bladder, drugs for relaxing the bladder cause constipation and mouth dryness and are therefore not tolerated well by the patients.

Diagnosis of bladder dysfunction requires continuously monitoring various bladder parameters during filling and/or voiding. These measurements usually are made by inserting a catheter connected to a measuring device into the bladder. This is done, for example, in uroflowmetry (measurement of urinary flow rate) which is non-invasive, simple and inexpensive. However, its sensitivity and specificity are low. Cystometry is an invasive technique for measuring bladder capacity, compliance and muscle tonus. Pressure-flow study is an invasive and costly test for distinguishing patients with low urinary flow due to obstruction or bladder antonia, from those with high intravesical pressure and high urinary flow. It is therefore a need in the art for a simple and inexpensive technique for intravesicular monitoring.

In the diagnostic procedure known as "urodynamics", the bladder is filled through a catheter, and the response of the bladder is monitored. Available 24 hour urodynamic monitors have catheters or wires passing through the urethra, connecting sensors inserted into the bladder to a recorder. The connecting wires and catheters inadvertently introduce pathogenic bacteria from the genital areas into the bladder. It is therefore desirable to be able to monitor bladder function over several cycles of filling and voiding without the need for such wires or catheters.

Diagnosis of some intravesical pathological conditions often involves inserting an endoscope into the bladder and optically scanning the bladder walls. In cases of bleeding in the ureters or the kidneys, the observation of blood coming through the ureteral orifices allows determination of the origin of the bleeding. However, if the bleeding has temporarily stopped at the time of the examination, or if the blood concentration in the urine is insufficient to make the urine red or pink, endoscopy is of little value in reaching a diagnosis. In such cases more invasive procedures are performed in order to enter the upper urinary tract. It is therefore desirable to be able to monitor the bladder over long periods of time.

Bladder shape during filling and its contraction during voiding is important for the diagnosis of certain bladder pathologies. These functions can be followed in fluoroscopy and by sonography. These techniques however are not accurate and cannot be used for monitoring changes in bladder shape over long periods of time. It would therefore be desirable to be able to continuously image the bladder interior over long periods of time.

The present invention therefore provides a device for continuous monitoring of the bladder interior and for the treatment of bladder disorders in which the disadvantages of the prior art devices are substantially reduced or eliminated.

SUMMARY OF THE INVENTION

The present invention provides system comprising a deformable plug, referred to herein as "an umbrella", for insertion into the urinary bladder. The umbrella is formed from a flexibly resilient material and may be used for the intermittent sealing of the urinary bladder outlet for the prevention of involuntary urine leakage. The umbrella is compressed prior to insertion and then allowed to expand after insertion in the bladder.

The invention may be used for the intermittent sealing of the urinary bladder outlet and the prevention of involuntary urine leakage. Sealing the urinary bladder outlet involves lodging the balloon in the outlet so as to seal it. Unsealing the outlet to allow voiding of the bladder involves dislodging the balloon from the outlet.

The invention may also be used for such purposes as for example, delivery of drugs, imaging the urinary bladder, and measuring intravesicular parameters such as pressure in the urinary bladder. When used for such purposes, the umbrella may be, for example, lodged in the urinary bladder outlet or immobilized in some other desired location in the bladder.

The invention is entirely confined to the urinary bladder and has no urethral parts. As will become apparent in the description below, the umbrella is easily inserted and removed. It may be left in the bladder for prolonged periods of time without encrusting or causing infections and is displaced within the bladder at will using a hand held magnet. The invention is comfortable for the patient and does not interfere with the daily activities of the patient including sitting, jogging, riding, or sexual intercourse.

The invention thus provides a device generally having an umbrella-like appearance formed from a flexibly resilient material for insertion into the urinary bladder of an individual, the device having a dome-shaped wall and a stem.

The invention also provides a system for treating urinary incontinence in an individual, the system comprising an umbrella-like device together with (a) an applicator for inserting the device into the urinary bladder of the individual or for removing the device from the individual's urinary bladder, the applicator adapted to releasably gripping the device; and (b) a magnetable displacing member for displacing the device within the urinary bladder.

The invention also provides a method for treating urinary incontinence in an individual comprising the steps of inserting an umbrella-like device into the individual's urinary bladder and (a) displacing the device into a sealing position for sealing the urinary bladder outlet; and (b) displacing the device within the urinary bladder into an unsealing position for voiding the urinary bladder.

A method for releasing one or more substances into the urinary bladder of an individual comprising the steps of loading the one or more substances into the wall or the stem of an umbrella device, and (a) inserting the device into the individual's urinary bladder;

(b) expanding the device in the urinary bladder; and (c) displacing the device within the urinary bladder to a desired location.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF SPECIFIC EMBODIMENTS

Figure 1:
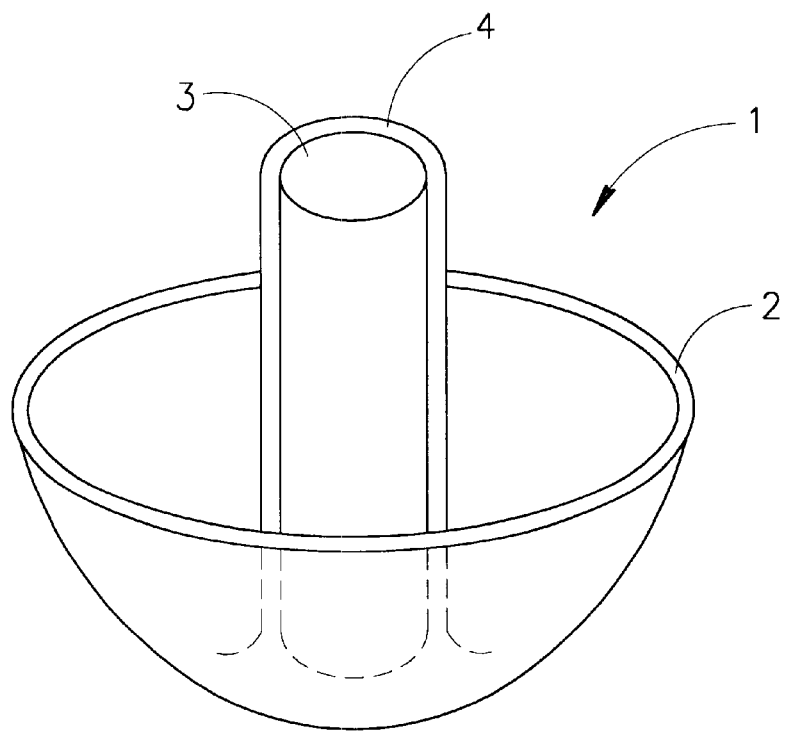
FIG. 1 shows an embodiment of the umbrella according to the invention.
Figure 1:
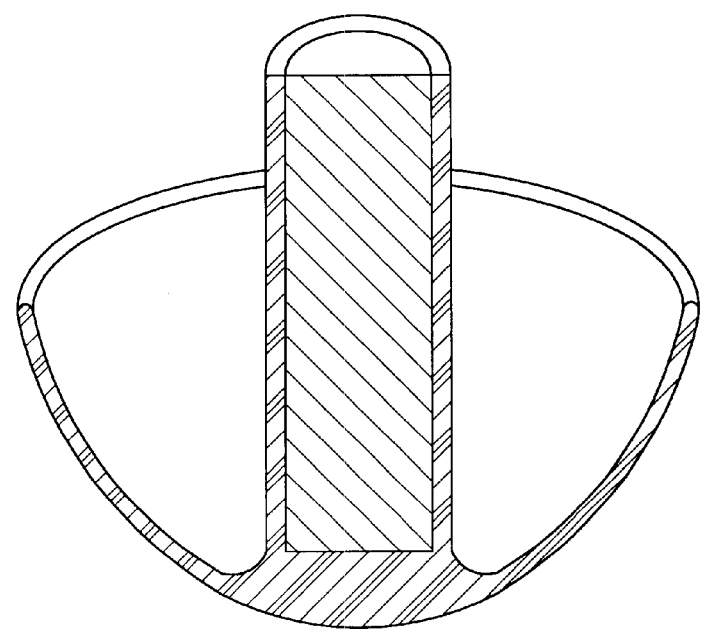

Reference is first made to FIG. 1 which shows an embodiment of the invention. An umbrella generally designated as 1 has a generally hemispherically shaped wall 2 and a stem 4 extending from the inner surface of wall 2. The umbrella is made of a resiliently flexible elastic biocompatible material. Umbrella 1 may optionally comprise a magnetable portion 3 which may consist for example, of one or more metal particles associated with stem 4 or wall 2 of the umbrella.

Figure 2A:
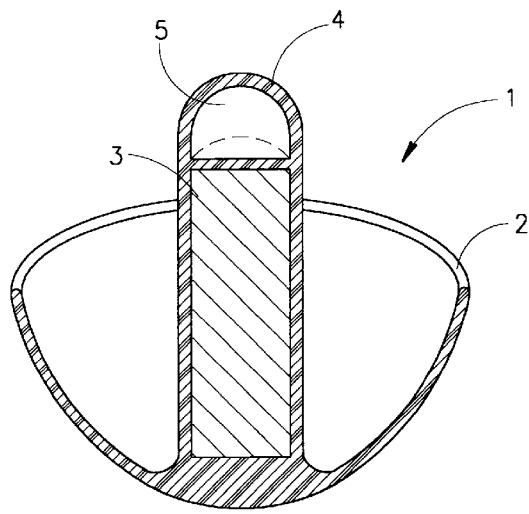
FIGS. 2(a–c) shows longitudinal sections of umbrellas having a chamber for storing substances.
Figure 2B:
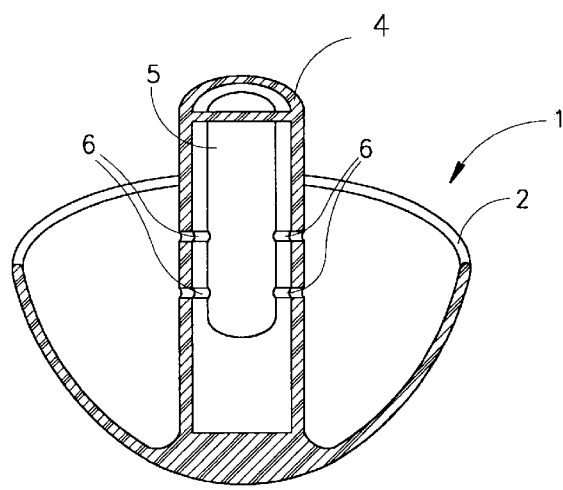
Figure 2C:
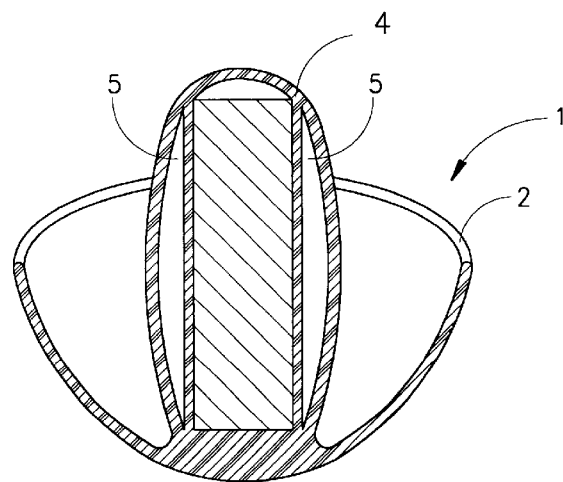

FIG. 2 shows three embodiments of the invention in cross section having one or more chambers 5 for storing one or more substances. Such substances could be, for example, drugs, antibiotics or radioactive substances, etc. The chamber 5 may be situated at the tip of the stem, as shown in FIG. 2a. In the embodiment of FIG. 2b, the chamber 5 is located within a hollow magnetable portion 3 and side ports 6 connect the interior of the chamber to the outer surface of magnetable portion 3. In FIG. 5c, chamber 5 is located around the magnetable portion 3. After insertion of the umbrella into the lumen of the urinary bladder, the substances diffuse from the umbrella 1 into the bladder in order to achieve a desired effect.

Figure 3:
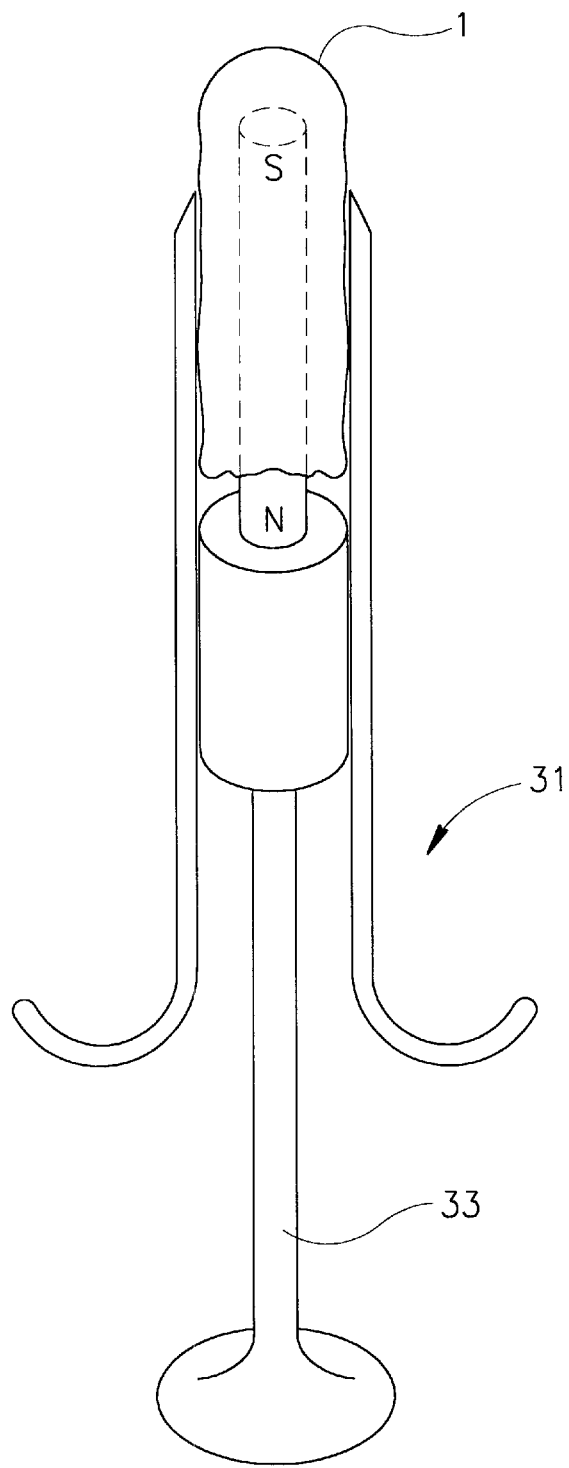
FIG. 3 shows an applicator for inserting an umbrella according to the invention into the urinary bladder of an individual.
Figure 4:
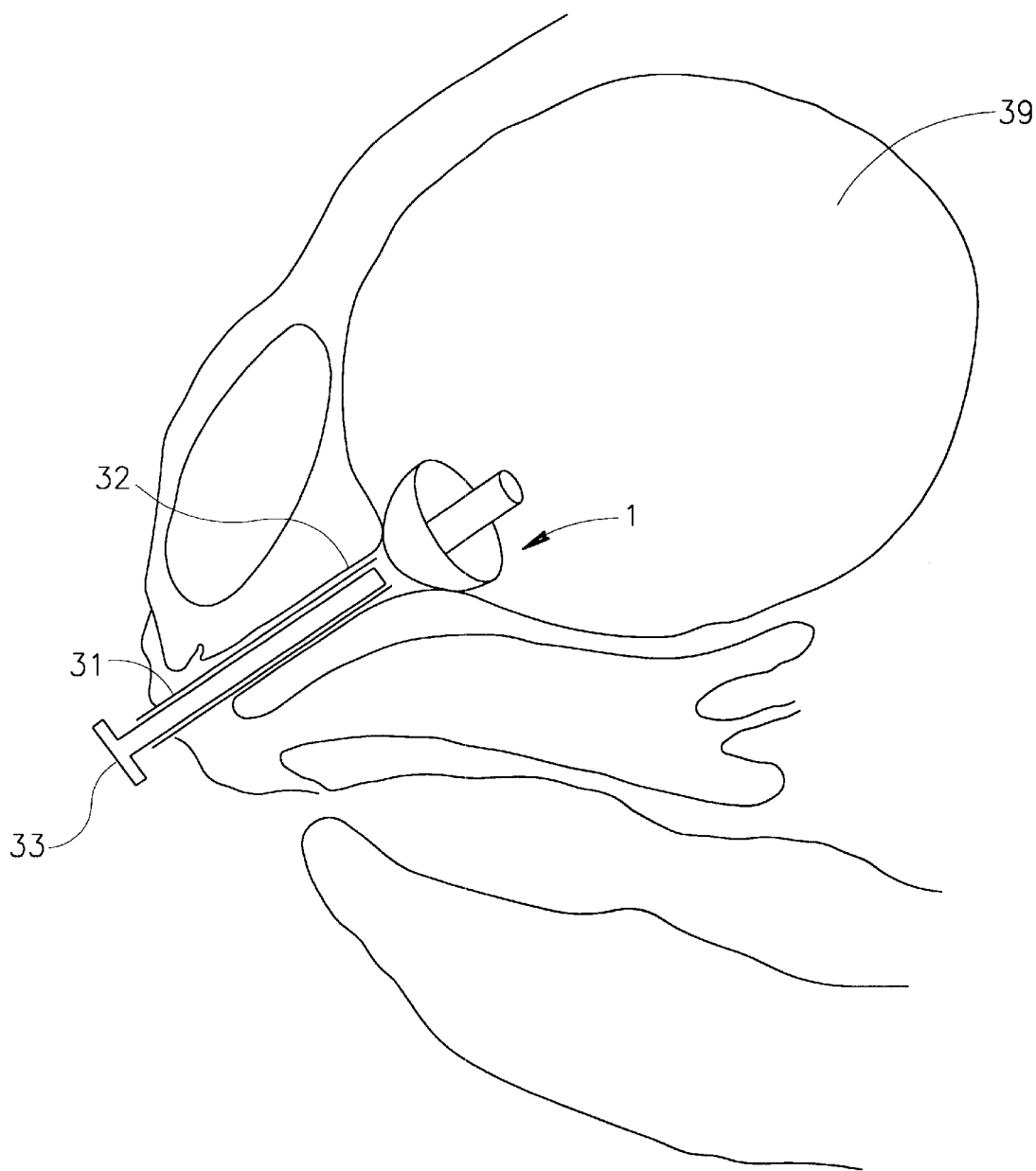
FIG. 4 shows an expanded umbrella being inserted into the urinary bladder with an applicator.

FIG. 3 shows an applicator 31 for inserting an umbrella into the lumen of the urinary bladder of an individual. When umbrella 1 is initially loaded into applicator it is maintained in a deformed state at the end of the applicator. As shown in FIG. 4, the distal end 32 of the applicator-umbrella combination is inserted into the urethra until it reaches the lumen of the bladder. The umbrella 1 is then released from the applicator by pushing the umbrella from applicator 31 with pushing piston 33. The applicator is then removed from the body, leaving the umbrella 1 in the bladder lumen 39. Following its release from the applicator into the bladder, the umbrella regains its initial shape.

Figures 5A, 5B:
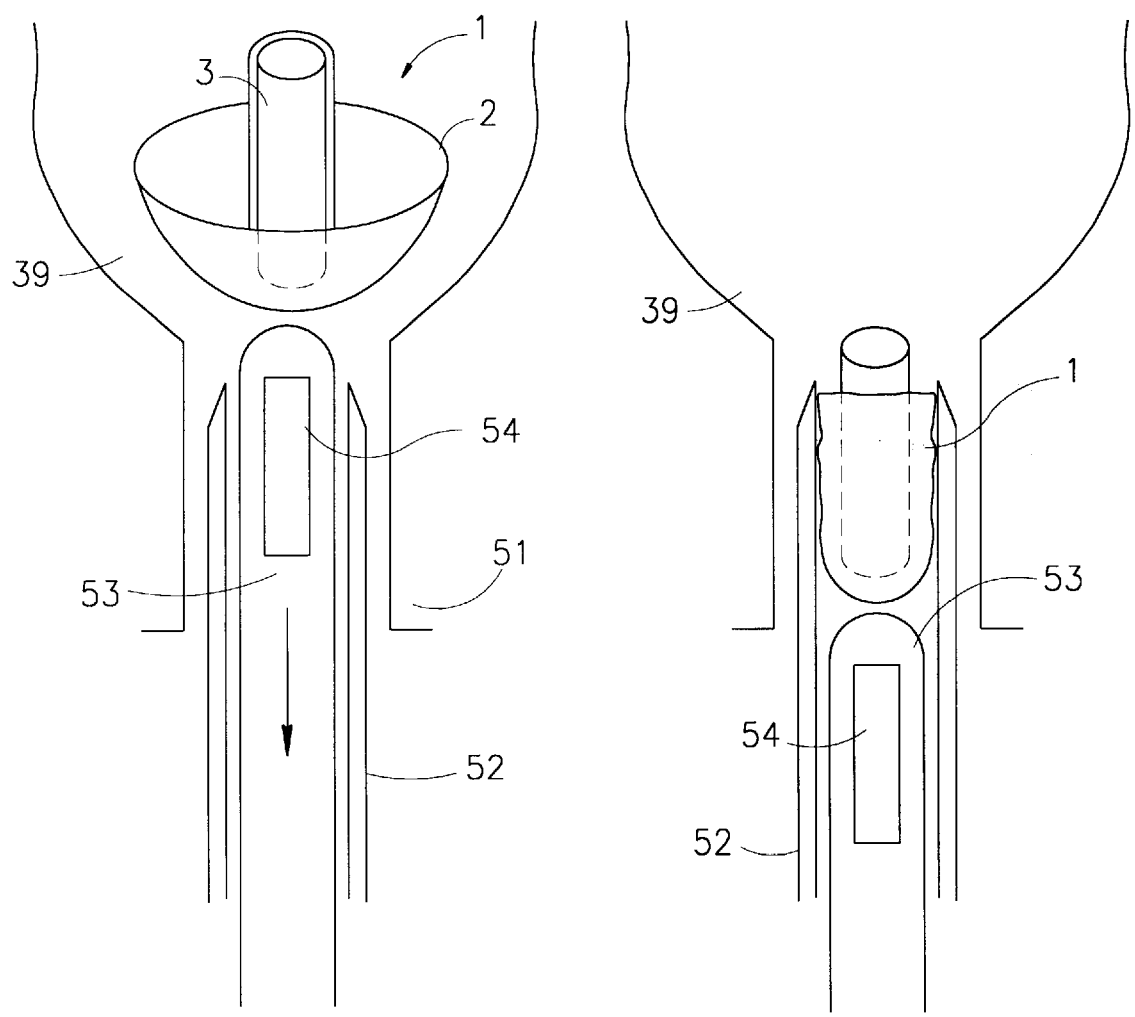
FIGS. 5(a–b) shows a retrieval device for retrieving the umbrella.

FIG. 5a shows a retrieval device generally designated 51 for removing the umbrella from the bladder 39. A catheter 52 has a probe 53 in its lumen which has at its distal end a magnetable portion 54 so as to engage an umbrella 1 at the distal tip by means of the magnetable portion 3 associated with the umbrella. As shown in FIG. 5b, when probe 53 is then retracted, umbrella 1 is deformed and brought into catheter 52. The retrieval device is then withdrawn from the patient together with the umbrella.

Figure 6:
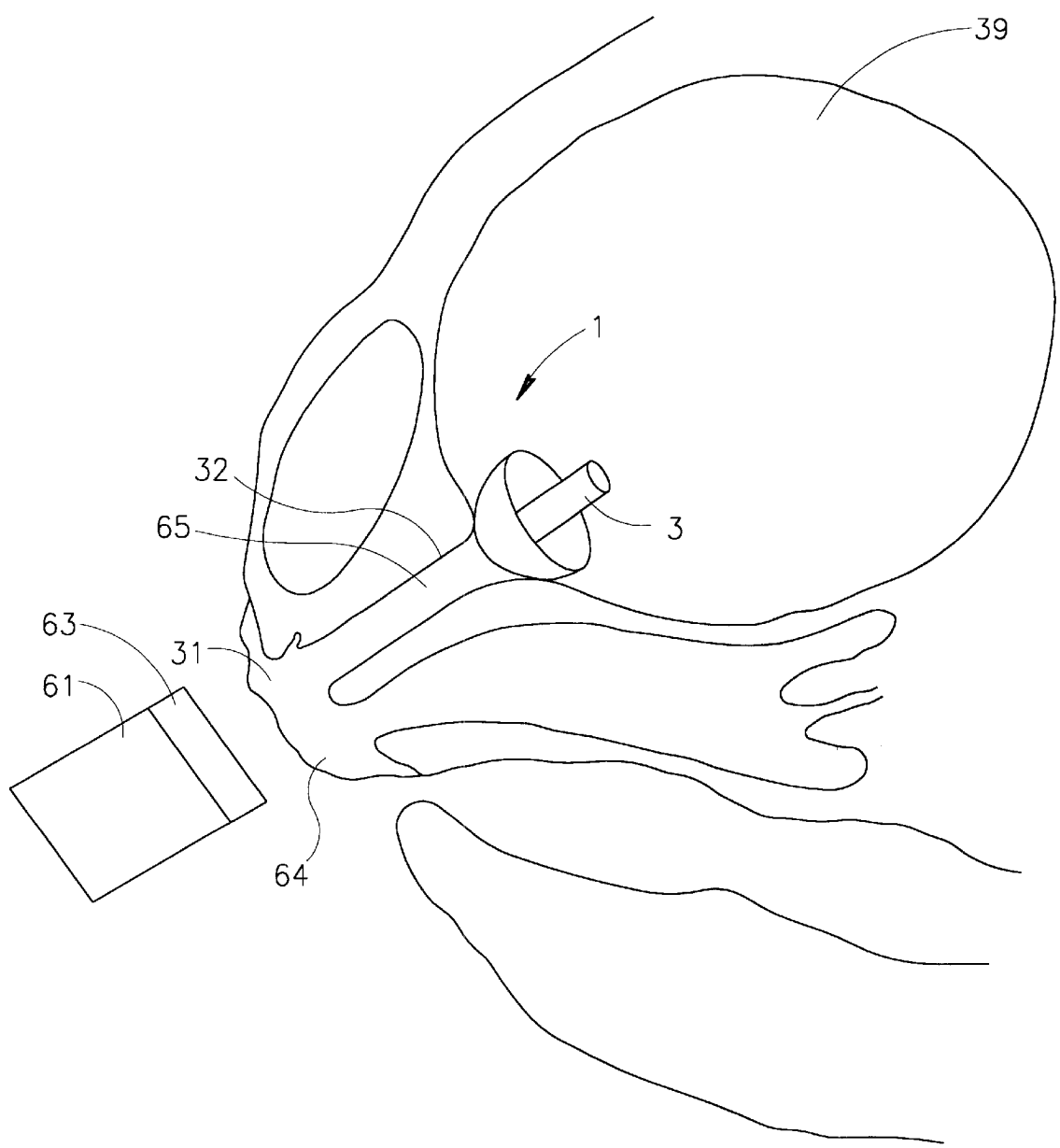
FIG. 6 shows use of a displacing member to displace the umbrella into a sealing position within the urinary bladder.
Figure 7:
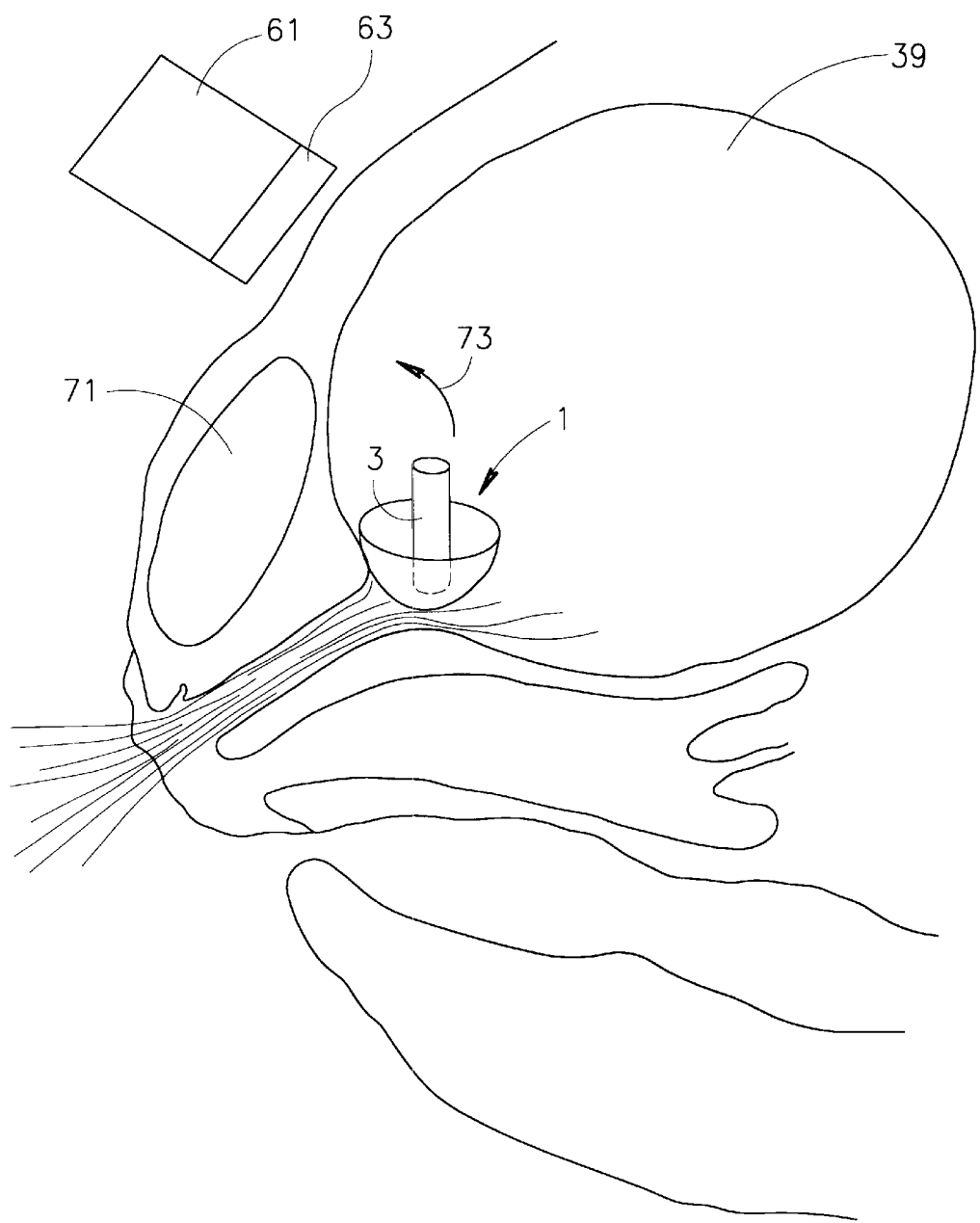
FIG. 7 shows use of a displacing member to displace the umbrella from a sealing position in the urinary bladder.

FIGS. 6 and 7 show use of a displacing member 61 to position an umbrella 1 having a magnetable portion 3 at a desired location within the lumen 62 of an individual's urinary bladder. Displacing member 61 is located outside the individual's body and comprises a magnetable portion 63. The displacing member is placed at a location on the surface of the individual's body so as to draw the umbrella from its initial location to the desired location.

FIG. 6 shows use of the umbrella for sealing the urinary bladder outlet in a female subject. Displacing member 61 is placed over the urethral meatus 64 such that, due to the magnetable portion 63 associated with displacing member 61 and the magnetable portion 3 associated with umbrella, the umbrella is drawn into the bladder outlet 65. The umbrella thus becomes lodged in the outlet and seals it. As the amount of urine in the bladder increases, a hydrostatic pressure is exerted on the umbrella further lodging it in the outlet and reinforcing the seal. The invention is used similarly for sealing the urinary bladder outlet in male subjects.

As seen in FIG. 7, in order to open the urinary bladder for voiding, magnetic displacing member 61 is placed over the upper edge of pubic bone 71. Due to the magnetable portion 3 of the umbrella, the umbrella is raised and dislodged from the bladder outlet so as to allow voiding of urine as indicated by arrow 73. After voiding, the umbrella is redrawn into the bladder outlet by the displacing member so as to seal the outlet again as shown in FIG. 6.

Figure 8:
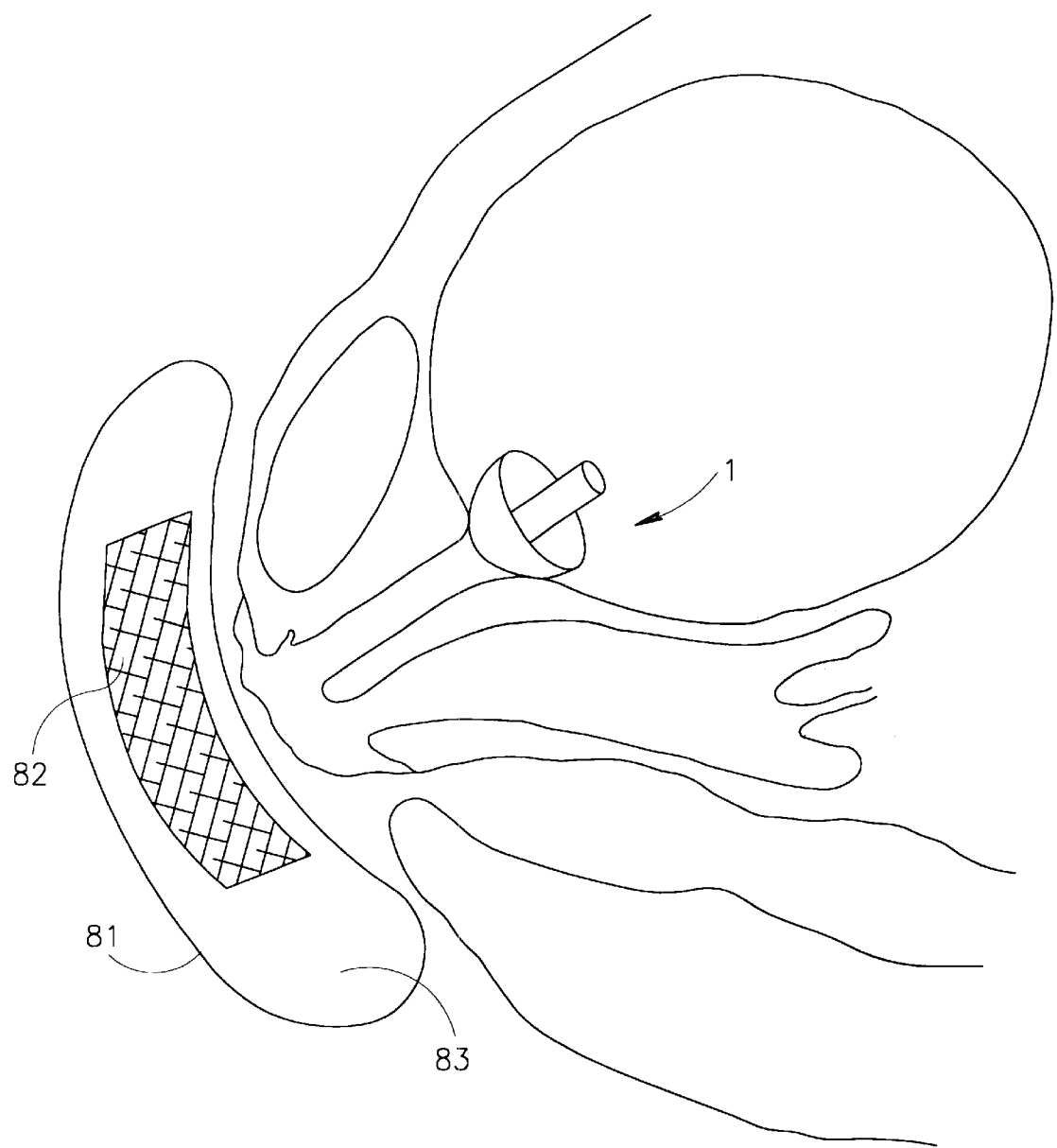
FIG. 8 shows use of an immobilizing member.

FIG. 8 shows use of an immobilizing member 81 comprising a magnetable portion 82 affixed to the surface of the individual's body so as to maintain umbrella 1 at a desired location in the lumen of the urinary bladder. Magnetable portion 82 of immobilizing member 81 may be enclosed in a coating 83 so as to form, for example, a hygienic pad. The immobilizing member may be affixed to the surface by means of tape, or by pressure applied to it by the individual's underwear.

The invention has been described with a certain degree of particularly only for the sake of clarity. However, several variations and modifications in the invention are possible without exceeding the scope and spirit of the invention as defined in the following set of claims.

What is claimed is:

1. A system for treating urinary incontinence in an individual, the system comprising:
    (a) a device comprising a resiliently flexible solid body for insertion into a urinary bladder wherein the body comprises a dome-shaped wall having a concave surface and a stem extending from the concave surface of the wall, the device being deformable so as to allow the entire device to pass through a urethra to the urinary bladder and to regain an umbrella-like appearance inside the bladder and said device having a magnetizable portion;
    (b) an applicator for inserting the device into the urinary bladder of the individual or for removing the device from the individual's urinary bladder, the applicator adapted to releasably grip the device;
    (c) a magnetizable displacing member for displacing the device within the urinary bladder and
    (d) an immobilizing member for immobilizing the device at a desired location in the individual's urinary bladder, comprising a magnetizable portion, said immobilizing member being adapted for being secured onto the individual's body.

2. The system according to claim 1, wherein the immobilizing member is in the form of a hygienic pad adapted to be placed in the individual's underwear.

3. The system of claim 1, wherein the applicator comprises a magnetizable portion for releasably gripping the device.

4. The system according to claim 1, for use in the treatment of a disorder selected from the list comprising:
    (a) urinary incontinence;
    (b) urinary bladder infections;
    (c) urinary bladder tumors; or
    (d) bladder dysfunction.

5. A method for treating urinary incontinence in an individual comprising the steps of:
    (a) inserting a device comprising a resiliently flexible solid body for insertion into a urinary bladder wherein the body comprises a dome-shaped wall having a concave surface and a stem extending from the concave surface of the wall, the device being deformable so as to allow the entire device to pass through a urethra to the urinary bladder and to regain an umbrella-like appearance inside the bladder and said device having a magnetizable portion, into the individual's urinary bladder;
    (b) displacing the device into a sealing position for sealing the urinary bladder outlet; and
    (c) displacing the device within the urinary bladder into an unsealing position for voiding the urinary bladder.

6. A method for releasing one or more substances into the urinary bladder of an individual comprising the steps of:
    (a) loading the one or more substances into the wall or the stem of a device that is capable of storing, one or more compounds and releasing then into the urinary bladder, said device comprising a resiliently flexible solid body for insertion into a urinary bladder wherein the body comprises a dome-shaped wall having a concave surface and a stem extending from the concave surface of the wall, the device being deformable so as to allow the entire device to pass through a urethra to the urinary bladder and to regain an umbrella-like appearance inside the bladder and said device having a magnetizable portion;
    (b) inserting the device into the individual's urinary bladder;
    (c) expanding the device into the urinary bladder; and
    (d) displacing the device within the urinary bladder to a desired location.

7. The method claim 6, wherein one or more of the one or more substance are selected from the list comprising:
    (a) drugs;
    (b) antibiotics; or
    (C) radioactive substances.

* * * * *